United States Patent
Nordquist et al.

(10) Patent No.: US 11,638,657 B2
(45) Date of Patent: May 2, 2023

(54) MEDICAL PLUG SYSTEM, METHOD, AND APPARATUS

(71) Applicant: Avent, Inc., Alpharetta, GA (US)

(72) Inventors: Jeffrey S. Nordquist, Lake Barrington, IL (US); Bernard Daurelle, Marseilles (FR)

(73) Assignee: Avent, Inc., Alpharetta, GA (US)

(*) Notice: Subject to any disclaimer, the term of this patent is extended or adjusted under 35 U.S.C. 154(b) by 922 days.

(21) Appl. No.: 16/464,078

(22) PCT Filed: Dec. 11, 2017

(86) PCT No.: PCT/US2017/065559
§ 371 (c)(1),
(2) Date: May 24, 2019

(87) PCT Pub. No.: WO2018/111755
PCT Pub. Date: Jun. 21, 2018

(65) Prior Publication Data
US 2019/0380861 A1   Dec. 19, 2019

Related U.S. Application Data

(60) Provisional application No. 62/435,216, filed on Dec. 16, 2016.

(51) Int. Cl.
*A61F 5/44* (2006.01)
*A61F 5/445* (2006.01)

(52) U.S. Cl.
CPC ............ *A61F 5/4407* (2013.01); *A61F 5/445* (2013.01)

(58) Field of Classification Search
CPC ........ A61F 5/4407; A61F 5/445; A61F 5/443; A61F 5/44
See application file for complete search history.

(56) References Cited

U.S. PATENT DOCUMENTS 2,243,529 A   5/1941   Grossman et al.
4,836,214 A   6/1989   Sramek
(Continued)

FOREIGN PATENT DOCUMENTS

EP   0 369 923 A1   5/1990
GB   2529922 A      3/2016
(Continued)

OTHER PUBLICATIONS

International Search Report and Written Opinion for PCT/US2017/065559, dated Mar. 6, 2018, 16 pages.

*Primary Examiner* — Guy K Townsend
(74) *Attorney, Agent, or Firm* — Dority & Manning, P.A.

(57) ABSTRACT

A medical plug apparatus for use in conjunction with an ostomy procedure includes a cap and an elongated cylindrical shaft. The cap has a top surface, a bottom surface, and a first thickness. The elongated cylindrical shaft extends orthogonally away from the bottom surface of the cap from a proximal end to a distal end and has shaft diameter and the shaft length adapted to plug a stoma cavity upon inserting the elongated cylindrical shaft into the stoma cavity. The cap includes a gripping portion that has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft.

20 Claims, 14 Drawing Sheets

(56) References Cited

U.S. PATENT DOCUMENTS

| | | | |
|---|---|---|---|
| 4,921,481 A | 5/1990 | Danis et al. | |
| 4,941,869 A * | 7/1990 | D'Amico | A61F 5/445 604/277 |
| 5,045,052 A * | 9/1991 | Sans | A61F 5/445 600/32 |
| 5,108,430 A * | 4/1992 | Ravo | A61F 2/04 623/23.68 |
| 5,125,897 A * | 6/1992 | Quinn | A61J 15/0065 604/99.03 |
| 6,036,673 A * | 3/2000 | Quinn | A61M 25/0068 604/174 |
| 6,334,064 B1 | 12/2001 | Fiddian-Green | |
| 6,357,447 B1 | 3/2002 | Swanson et al. | |
| 6,451,883 B1 * | 9/2002 | Chen | A61L 15/585 524/25 |
| 6,485,476 B1 * | 11/2002 | von Dyck | A61F 5/441 604/332 |
| 6,540,724 B1 * | 4/2003 | Harris | A61M 25/02 607/104 |
| 7,780,639 B2 * | 8/2010 | Van Lue | A61B 17/3462 604/264 |
| 7,818,155 B2 | 10/2010 | Stuebe et al. | |
| 8,147,486 B2 | 4/2012 | Honour et al. | |
| 8,388,586 B2 * | 3/2013 | Weig | A61F 5/445 604/338 |
| 8,613,702 B2 | 12/2013 | Feer et al. | |
| 8,777,912 B2 * | 7/2014 | Nishtala | A61M 3/0283 604/327 |
| 8,986,230 B2 | 3/2015 | Nishtaia | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,345,612 B2 * | 5/2016 | Hanuka | A61F 5/4404 |
| 9,517,157 B2 * | 12/2016 | Hanuka | A61F 5/4401 |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 | 7/2017 | Elia et al. | |
| 9,883,964 B2 * | 2/2018 | Hanuka | A61F 5/441 |
| 10,071,234 B2 * | 9/2018 | Koelper | A61M 39/1011 |
| 10,441,455 B2 * | 10/2019 | Eggert | A61F 5/4405 |
| 10,524,953 B2 * | 1/2020 | Hanuka | A61F 5/445 |
| 10,786,652 B2 * | 9/2020 | Doshi | A61F 13/0226 |
| 10,966,907 B2 * | 4/2021 | Puckett | A61J 3/07 |
| 11,224,732 B2 * | 1/2022 | Nordquist | A61J 15/0026 |
| 11,395,757 B2 * | 7/2022 | Eggert | A61F 5/445 |
| 2003/0040768 A1 * | 2/2003 | Greene | A61B 17/0057 606/190 |
| 2003/0204174 A1 | 10/2003 | Cisko, Jr. | |
| 2006/0224131 A1 * | 10/2006 | Calvert | A61J 15/0026 604/344 |
| 2007/0142780 A1 * | 6/2007 | Van Lue | A61B 17/3462 604/167.01 |
| 2008/0097179 A1 | 4/2008 | Russo | |
| 2008/0167607 A1 | 7/2008 | Pfeiffer et al. | |
| 2008/0249467 A1 | 10/2008 | Burnett et al. | |
| 2010/0069859 A1 * | 3/2010 | Weig | A61F 5/445 604/335 |
| 2010/0280489 A1 * | 11/2010 | Nishtala | A61M 3/0287 604/514 |
| 2011/0282311 A1 * | 11/2011 | Nishtala | A61F 5/4405 604/332 |
| 2012/0016256 A1 | 1/2012 | Mabary et al. | |
| 2012/0277619 A1 | 11/2012 | Starkebaum et al. | |
| 2013/0225946 A1 | 8/2013 | Feer et al. | |
| 2013/0304008 A1 * | 11/2013 | Hanuka | B31B 50/26 604/338 |
| 2015/0094675 A1 * | 4/2015 | Kyvik | A61F 5/443 604/337 |
| 2016/0113843 A1 | 4/2016 | Elia et al. | |
| 2016/0129223 A1 | 5/2016 | Kirschenman | |
| 2016/0143815 A1 * | 5/2016 | Koelper | A61M 39/105 604/533 |
| 2016/0256665 A1 * | 9/2016 | Doshi | A61F 13/00063 |
| 2016/0287428 A1 * | 10/2016 | Eggert | A61F 5/445 |
| 2016/0325088 A1 * | 11/2016 | Nordquist | A61B 90/70 |
| 2016/0331298 A1 | 11/2016 | Burnett et al. | |
| 2017/0071502 A1 | 3/2017 | Bennett-Guerrero | |
| 2017/0202750 A1 | 7/2017 | Elia | |
| 2018/0078195 A1 | 3/2018 | Sutaria et al. | |
| 2018/0161249 A1 | 6/2018 | Elia et al. | |
| 2018/0289536 A1 | 10/2018 | Burnett | |

FOREIGN PATENT DOCUMENTS

| | | |
|---|---|---|
| JP | 2001514051 A | 9/2001 |
| SU | 1099958 A1 | 6/1984 |
| WO | WO 90/07311 A1 | 7/1990 |
| WO | WO 92/17150 | 10/1992 |
| WO | WO 99/11302 A1 | 3/1999 |

* cited by examiner

MEDICAL PLUG SYSTEM, METHOD, AND APPARATUS

RELATED APPLICATION

The present application is tile national stage entry of International Patent Application No. PCT/US2017/065559, having a filing date of Dec. 11, 2017, which claims priority to U.S. Provisional Application Ser. No. 62/435,216, filed on Dec. 16, 2016, both of which are incorporated herein in their entirety by reference thereto.

BACKGROUND

The present disclosure relates to procedures, such as ostomy procedures, where an opening is surgically created in the body for the discharge of body fluid. Some example procedures include colostomy (artificial opening created in abdominal wall to bypass a damaged part of the colon), ileostomy (piece of ileum is diverted to an artificial opening created in abdominal wall), urostomy (artificial opening creating for the urinary system), esophagostomy (artificial opening created in esophagus, such as the cervical section of the esophagus), gastrostomy (artificial opening created in the stomach), etc. For example, the opening may allow waste to be removed from the body. The surgically created openings may result in a stoma, which may be temporary or permanent. The stoma may be used to allow other portions of the body to rest or heal. These procedures require closing devices (traditionally a clamp or tail clip), which close the stoma in-between catheter or bag insertions and other medical procedures.

SUMMARY

The present disclosure provides a new and innovative system, method, and apparatus for a medical plug. In an exemplary aspect of the present disclosure, a medical plug apparatus for use in conjunction with an ostomy procedure includes a cap and a flexible, elongated cylindrical shaft. The cap has a top surface, a bottom surface, and a first thickness. The elongated cylindrical shaft extends orthogonally away from the bottom surface of the cap from a proximal end to a distal end. The first thickness extends from the top surface to the bottom surface at the proximal end of the elongated cylindrical shaft. Additionally, the elongated cylindrical shaft has a smooth external surface, a shaft diameter, and a shaft length. The shaft diameter and the shaft length are adapted to plug a stoma cavity upon inserting the elongated cylindrical shaft into the stoma cavity. The bottom surface of the cap includes a gripping portion, a contact portion, and a shoulder between the gripping portion and the contact portion. The shoulder extends around a periphery of the contact portion. The gripping portion includes a first region, a second region, and a second thickness, which extends from the top surface to the gripping portion at the shoulder. Additionally, the gripping portion extends from the top surface towards the bottom surface. The second thickness is less than the first thickness, and the gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft. The contact portion includes a contact diameter, the contact portion extends from the shoulder across the bottom surface of the cap to the proximal end of the elongated cylindrical shaft. The shoulder includes a third thickness, which extends from the gripping portion at the shoulder to the contact portion and the third thickness is less than the first thickness. The gripping diameter is larger than the contact diameter, and the contact portion is adapted to create a seal with a layer of skin of a patient.

In accordance with another exemplary aspect of the present disclosure, a stoma assembly includes a medical plug and a flexible bandage. The medical plug includes a cap and a flexible, elongated cylindrical shaft. The cap has a top surface, a bottom surface, and a first thickness. The elongated cylindrical shaft extends orthogonally away from the bottom surface of the cap from a proximal end to a distal end. The first thickness extends from the top surface to the bottom surface at the proximal end of the elongated cylindrical shaft. Additionally, the elongated cylindrical shaft has a smooth external surface, a shaft diameter, and a shaft length. The shaft diameter and the shaft length are adapted to plug a stoma cavity upon inserting the elongated cylindrical shaft into the stoma cavity. The bottom surface of the cap includes a gripping portion, a contact portion, and a shoulder between the gripping portion and the contact portion. The shoulder extends around a periphery of the contact portion. The gripping portion includes a first region, a second region, and a second thickness, which extends from the top surface to the gripping portion at the shoulder. Additionally, the gripping portion extends from the top surface towards the bottom surface. The second thickness is less than the first thickness, and the gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft. The contact portion includes a contact diameter, the contact portion extends from the shoulder across the bottom surface of the cap to the proximal end of the elongated cylindrical shaft. The shoulder includes a third thickness, which extends from the gripping portion at the shoulder to the contact portion and the third thickness is less than the first thickness. The gripping diameter is larger than the contact diameter, and the contact portion is adapted to create a seal with a layer of skin of a patient. The flexible bandage has an attachment side and an exterior side. The attachment side includes an adhesive coating and the exterior side is smooth. Additionally, the flexible bandage has a size and shape that is adapted to completely cover the cap of the medical plug. The flexible bandage includes a peripheral portion extending beyond the entire outside edge of the cap. The adhesive coating on the attachment side of the peripheral portion enables the flexible bandage to adhere to the patient and form a barrier between the outside edge of the cap and the outside environment.

In accordance with another exemplary aspect of the present disclosure, a medical plug apparatus for use in conjunction with an ostomy procedure, the medical plug apparatus includes a cap and a flexible, elongated cylindrical shaft. The cap has an outside edge, a top surface and a bottom surface. The cylindrical shaft extends orthogonally away from the bottom surface of the cap from a proximal end to a distal end. The elongated cylindrical shaft has a smooth external surface, a predetermined diameter, and a shaft length. The shaft diameter and the shaft length are adapted to plug a stoma cavity upon inserting the elongated cylindrical shaft into the stoma cavity. The top surface of the cap includes a gripping member, and the gripping member includes a raised protrusion extending along a diameter of the cap. Additionally, the gripping member is adapted to transfer a rotational force in a twisting action to dislodge the medical plug and facilitate removal of the medical plug apparatus such that upon exerting a pulling force on the gripping member, the elongated cylindrical shaft is directed outwardly away from the patient by the pulling force causing a substantially axial tension force on the elongated cylindrical shaft, and the bottom surface is adapted to create a seal with a layer of skin of a patient.

In accordance with another exemplary aspect of the present disclosure, a method includes positioning a flexible, elongated cylindrical shaft of a medical plug over a stoma cavity of a patient, and inserting the elongated cylindrical shaft of the medical plug into the stoma cavity of a patient. The medical plug includes a cap having a top surface, a bottom surface, and a first thickness. The elongated cylindrical shaft extends orthogonally away from the bottom surface of the cap from a proximal end to a distal end. Additionally, the first thickness extends from the top surface to the bottom surface at the proximal end of the elongated cylindrical shaft. The elongated cylindrical shaft has a smooth external surface, a shaft diameter, and a shaft length, where the shaft diameter and the shaft length adapted to plug a stoma cavity upon inserting the elongated cylindrical shaft into the stoma cavity. The bottom surface of the cap includes a gripping portion, a contact portion, and a shoulder between the gripping portion and the contact portion. The shoulder extends around a periphery of the contact portion. Additionally, the method includes positioning the contact portion of the cap into close contact with the patient's skin by applying a downward pressure to the top surface of the cap. The contact portion includes a contact diameter, and the contact portion extends from the shoulder across the bottom surface of the cap to the proximal end of the elongated cylindrical shaft. The shoulder includes a third thickness, which extends from the gripping portion at the shoulder to the contact portion and is less than the first thickness. Additionally, the contact portion is adapted to create a seal with a layer of skin of a patient. The gripping portion includes a first region, a second region, and a second thickness. Further, the gripping portion extends from the top surface towards the bottom surface, and the second thickness extends from the top surface to the gripping portion at the shoulder. The second thickness is less than the first thickness. The method also includes exerting a pulling force on the first region and the second region of the gripping portion, to direct the elongated cylindrical shaft outward and away from the patient. The gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft. The gripping diameter is larger than the contact diameter.

Additional features and advantages of the disclosed system, method, and apparatus are described in, and will be apparent from, the following Detailed Description and the Figures.

DETAILED DESCRIPTION OF EXAMPLE EMBODIMENTS

Figure 1:
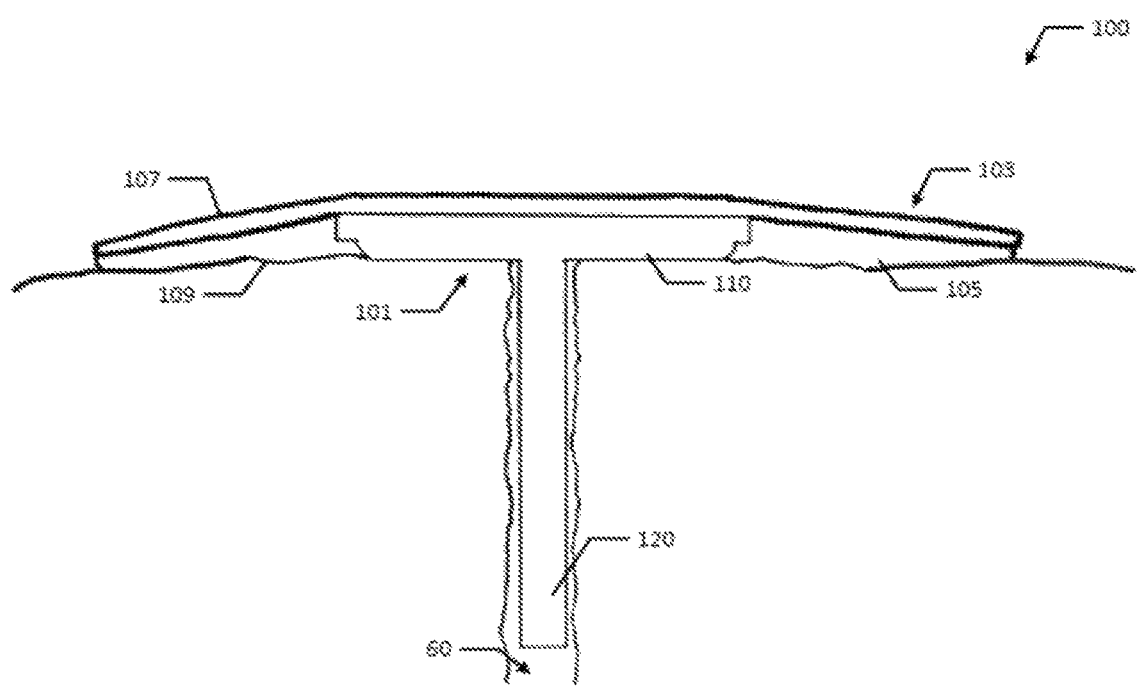
FIG. 1 is a side view of a stoma assembly, according to an example embodiment of the present disclosure.

Referring to the Figures, embodiments of an enteral feeding and gastric pressure relief/suction device are disclosed. As seen in an exemplary stoma assembly 100 illustrated in FIG. 1, the stoma assembly 100 includes a medical plug 101 and a flexible bandage 103. The medical plug 101 is for use in conjunction with an ostomy procedure. For example, the medical plug 101 includes a cap 110 and an elongated cylindrical shaft 120 that may be adapted to plug a stoma cavity 60 of a patient. Additionally, the cap 110 may be adapted to create a seal with a layer of skin of the patient. The flexible bandage 103 may also aid in sealing the stoma cavity 60 from the outside environment. For example, the flexible bandage 103 includes an attachment side 105 and an exterior side 107. The attachment side 105 may include an adhesive coating 109 that enables the flexible bandage 103 to adhere to the patient and form a barrier between the cap 110 and the outside environment.

Figure 2:
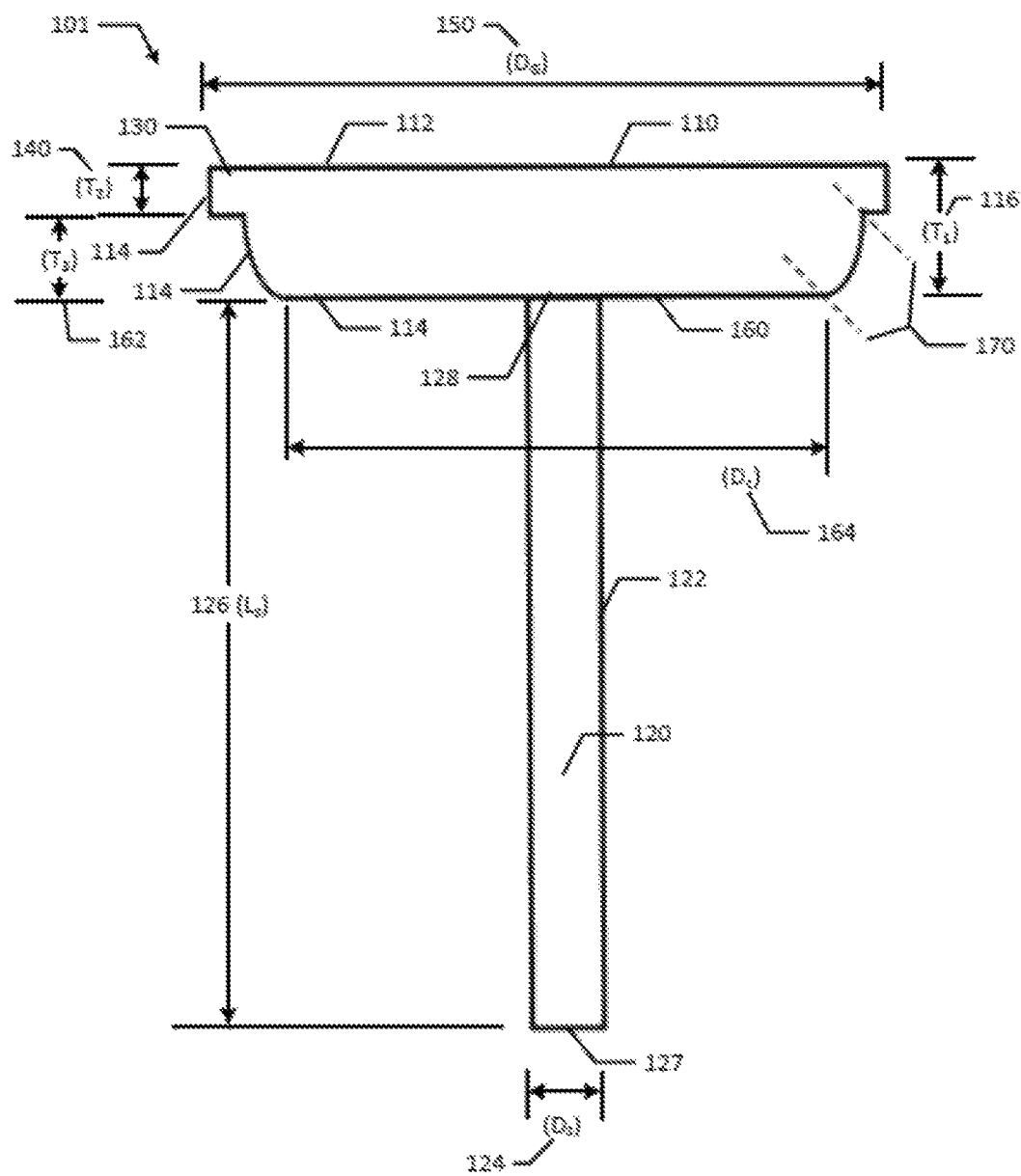
FIG. 2 is a side view of a medical plug, according to an example embodiment of the present disclosure.

FIG. 2 illustrates an example embodiment of a medical plug apparatus 101. The medical plug apparatus 101 includes a cap 110 and a flexible, elongated cylindrical shaft 120. The cap 110 has a top surface 112, a bottom surface 114, and a first thickness 116. For example, the top surface 112 of the cap 110 is the surface exposed to the outside environment when the cap 110 is placed in the stoma cavity 60 of a patient. The bottom surface 114 may include the sides of the cap 110 and the bottom face of the cap 110 (e.g., all surfaces that are not the top surface 112). The cap 110 of the medical plug apparatus 101 may have a round shape. In another example embodiment, the cap 110 may have a rectangular or square shape. Additionally, the cap may be symmetrical. In other embodiments, the cap may be asymmetrical. Additionally, the cap 110 has a first thickness 116 that extends from the top surface 112 to the bottom surface 114. In an example embodiment, the first thickness 116 may range between 0.05 inches to 0.2 inches.

In an example embodiment, the medical plug 101 may be made from a single mold or multiple molds. Additionally, the medical plug 101 may be made from polyurethane, silicone, or the like, which advantageously provide sufficient flexibility, durability, chemical resistant properties, and ease of molding. In another example embodiment, the medical plug 101 may be made from polyurethane. If the medical plug 101 is made from multiple molds, the cap 110 and the elongated cylindrical shaft 120 may be bonded together using adhesive, solvent bonding, radio-frequency (RF) welding and/or any other suitable means of affixing. The cylindrical shaft 120 may be adapted to maintain stoma patency and help prevent stoma stenosis (closing or tightening of the stoma). For example, the cylindrical shaft 120 may have sufficient strength and rigidity to prevent the stoma from tightening or closing.

In an example embodiment, the bottom surface 114 of the cap 110 includes a gripping portion 130. The gripping portion 130 may include a gripping diameter ($D_G$) 150. Additionally, the gripping portion 130 may have a second thickness 140 that extends from the top surface of the cap toward the bottom surface. The second thickness 140 is less than the first thickness 116. In an example embodiment the second thickness 140 may be between 0.03 and 0.15 inches. Additionally, the bottom surface 114 may include a contact portion 160 and a shoulder 170 between the gripping portion 130 and the contact portion 160. In the example with the contact portion 160 and the shoulder 170, the second thickness 140 may extend from the top surface 112 to the gripping portion 130 at the shoulder 170. For example, the shoulder 170 may extend around a periphery 136 (as illustrated in FIGS. 3A-E) of the contact portion 160. The shoulder 170 may provide a gradual transition between the contact portion 160 and the gripping portion 130. In an example embodiment, the shoulder 170 may provide a stepped transition between the contact portion 160 and the gripping portion 130. In another example embodiment, the shoulder 170 may include a curved or rounded transition at the contact portion 160 and may meet at an edge at the bottom of the gripping portion 130. In another example embodiment, the shoulder 170 may include a curved or rounded transition at both the contact portion 160 and the gripping portion 130.

In an example, the contact portion 160 extends from the shoulder 170 across the bottom surface 114 of the cap 110 to the proximal end 128 of the elongated cylindrical shaft 120. The contact portion 160 may include a contact diameter ($D_C$) 164. Additionally, the shoulder 170 includes a third thickness 162, which extends from the gripping portion 130 at the shoulder 170 to the contact portion 160. In an example, the third thickness 162 is less than the first thickness 116. Additionally, the gripping diameter ($D_G$) 150 is larger than the contact diameter ($D_C$) 164. In an example, the contact portion 160 is adapted to create a seal with a layer of skin of a patient.

Figure 3A:
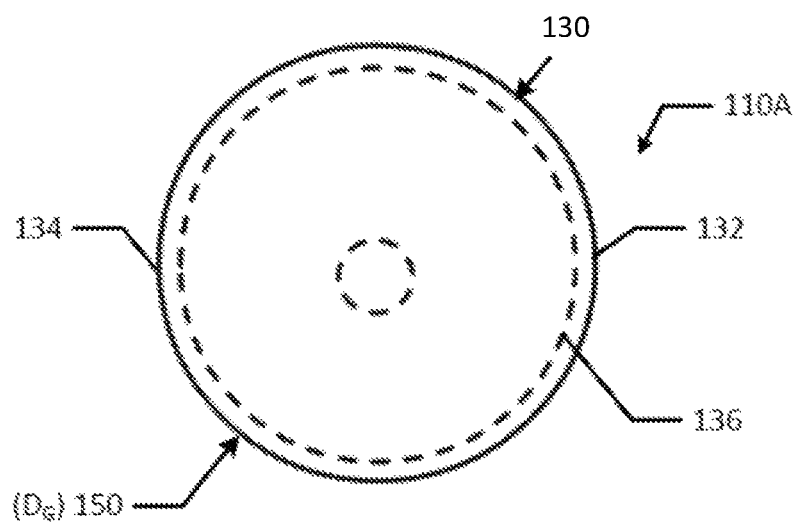
FIGS. 3A to 3E are top views of a medical plug cap, according to an example embodiment of the present disclosure.
Figure 3B:
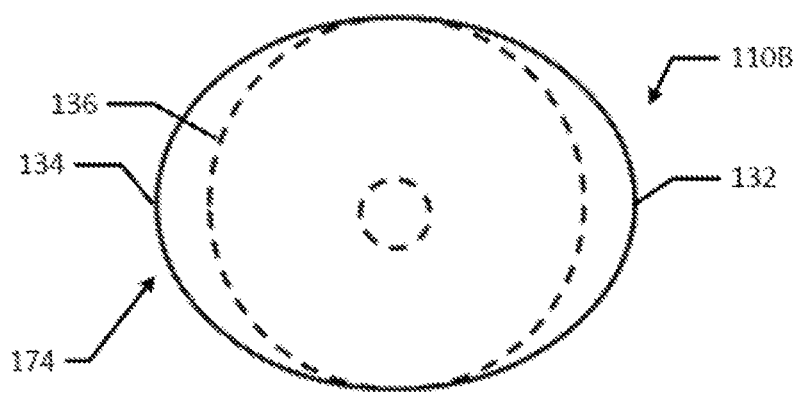
Figure 3C:
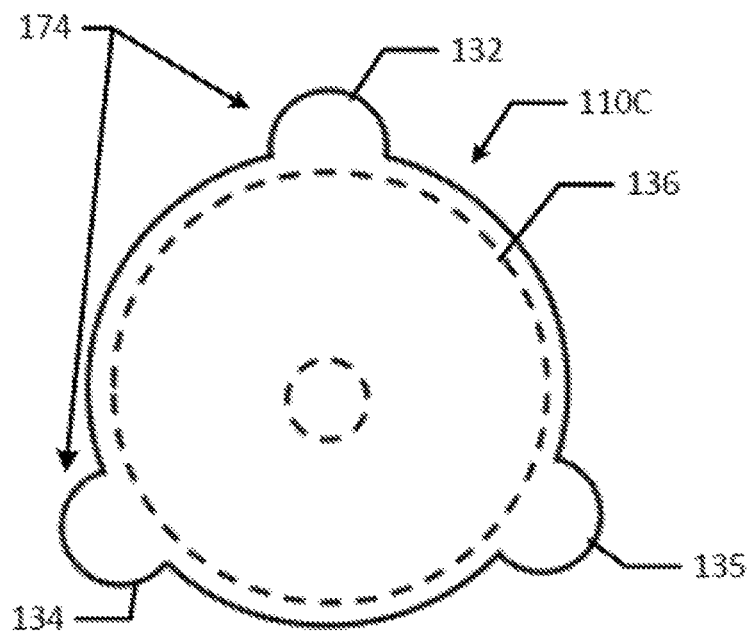
Figure 3D:
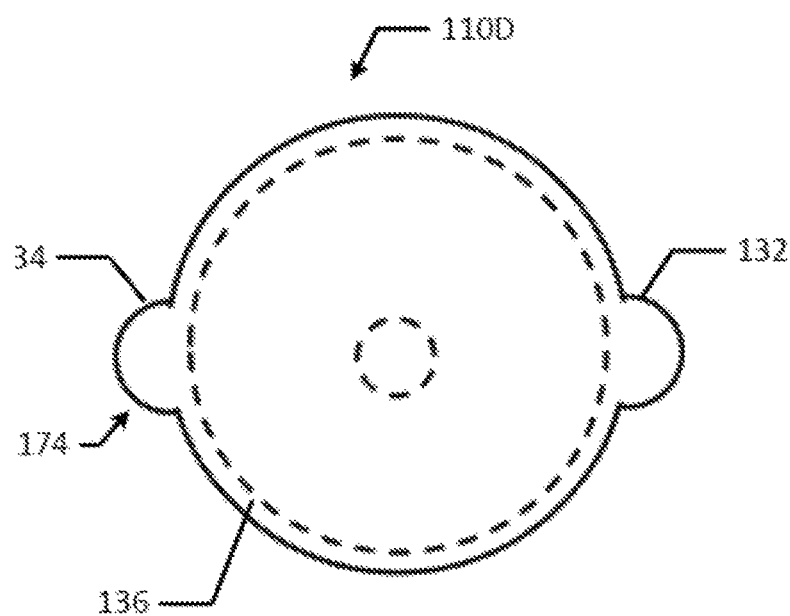
Figure 3E:
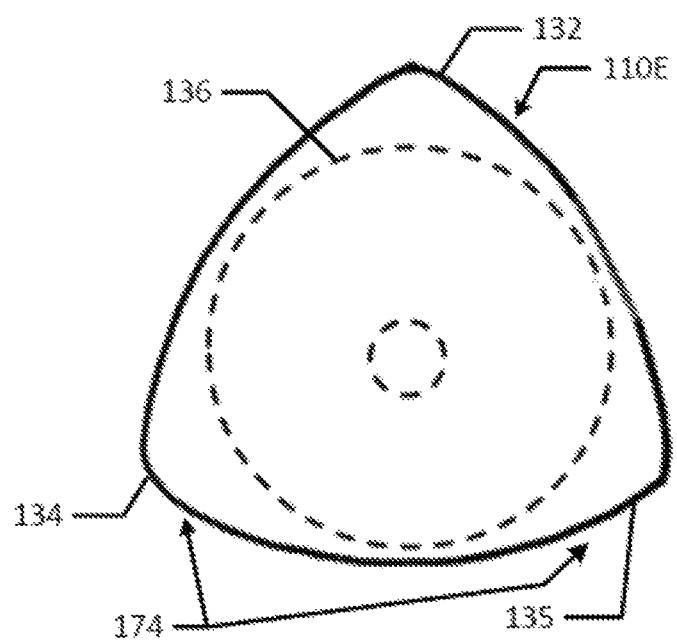

As further illustrated in FIGS. 3A through 3E, the gripping portion 130 may include one or more regions for gripping the medical plug 101. In an example embodiment, the gripping portion 130 may include a first region 132 and a second region 134. Additionally, the gripping portion may include other regions, such as a third region 135 (e.g., region that may be gripped by middle finger). For example, the gripping portion 130 may form a lip around the periphery of the cap 110 that includes a first region 132 (e.g., region that may be gripped by index finger) and a second region 134 (e.g., region that may be gripped by thumb). As illustrated in FIG. 3A, the gripping portion 130 has a gripping diameter ($D_G$) 150 that is larger than the contact portion 160 of the cap 110A (generally referred to as cap 110). In the example embodiment in FIG. 3A, the gripping portion 130 may be symmetric about the contact portion 160 and/or the cylindrical shaft 120. In another example embodiment, the gripping portion 130 may include two pronounced regions (e.g., a first region 132 and a second region 134) that extend beyond the contact portion 160. For example, as illustrated in FIG. 3B, the gripping portion 130 may have an oval shape to provide a lip or flange on the cap 110B (generally referred to as cap 110). The lip or flange advantageously increases the surface area of the gripping portion 130 to aid a clinician or patient in inserting or removing the medical plug 101. As illustrated in FIG. 3B, the shoulder 170 of the first flange 174 may be separate from a second shoulder of a second flange 174. In other example embodiments, the gripping portion 130 may have the shape of as a square, a triangular shape (as illustrated in FIG. 3E), or the like. Additionally, the gripping portion 130 may include one or more flanges or tabs 174 to provide additional structure to grip on the cap 110. For example, the cap 110D may include two flanges 174 (as illustrated in FIG. 3D). In another example embodiment, the cap 110C may include three flanges 174 (as illustrated in FIG. 3C). The flanges 174 may be spaced equidistant axially about the perimeter of the cap 110, for example, as provided in cap 110B, and similarly provided in caps 110C, 110D, and 110E. In other example embodiments, the flanges 174 may have uneven spacing about the perimeter of the cap 110. For example, the flanges 174 may be spaced such that they are comfortably accessible by a clinician or patient's index finger, thumb, middle finger, etc.

The elongated cylindrical shaft 120 extends orthogonally away from the bottom surface 114 of the cap 110 from a proximal end 128 to a distal end 127. For example, the distal end 127 of the cylindrical shaft 120 is the end that is first inserted into the stoma cavity 60 of a patient (e.g., the furthest extending end beneath the skin of the patient). In an example embodiment, the distal end 127 of the cylindrical shaft 120 may be rounded to aid in insertion, removal, and to prevent injury or irritation. Additionally, the elongated cylindrical shaft 120 may have a smooth external surface 122 to prevent injury when inserting and removing the medical plug 101 from the patient. For example, a stiff or rough cylindrical shaft 120 may cause serious problems including necrosis, damage to the stoma cavity 60, or cause the patient other irritation and discomfort or injury. The cylindrical shaft 120 includes a shaft diameter ($D_S$) 124 and a shaft length ($L_S$) 126. The shaft diameter ($D_S$) 124 and the shaft length ($L_S$) 126 are adapted to plug a stoma cavity. For example, upon inserting the elongated cylindrical shaft 120 into the stoma cavity 60, the shaft length ($L_S$) 126 is adapted to plug the stoma at a required depth. Additionally, the shaft diameter ($D_S$) 124 is adapted to plug the cavity diameter of the stoma cavity 60. In an example embodiment, the shaft diameter ($D_S$) 124 may range from size 5 French (e.g., 5 FR) to size 18 French (e.g., 18 FR). In other example embodiments, the shaft diameter ($D_S$) 124 may depend on the patient's age, weight, gender, etc. Additionally, the shaft diameter ($D_S$) 124 may depend on the type of medical procedure performed on the patient. Similarly, the shaft length ($L_S$) 126 may depend on the patient's age, weight, gender, etc. In another example embodiment, the shaft length ($L_S$) 126 may depend on the type of medical procedure performed on the patient. The shaft length ($L_S$) 126 may range from 0.5 to 2.5 inches.

FIGS. 4A through 4D illustrate example embodiments of a medical plug apparatus 101. The medical plug apparatus 101A-B (generally referred to as medical plug 101) may include a cap 110 with an outside edge 172. Additionally, the top surface 112 of the cap 110 may include a gripping member 200. In other example embodiments, the top surface 112 of the cap 110 may be textured. For example, the medical plug 101 may include a top surface that is embossed or debossed. The entire top surface 112 of the cap 110 may be textured. In other example embodiments, only a portion of the top surface 112 of the cap 110 may be textured (e.g., embossed, debossed, etc.). The gripping member 200 may include a raised protrusion 202 that extends along a diameter of the cap. The raised protrusion 202 may have a height ($H_P$) 220 such that it provides additional grip without overly increasing the profile of the cap 110. For example, the height ($H_P$) 220 may be configured such that the raised protrusion 202 provides adequate grip without reducing the ability of the bandage 103 to seal the medical plug 101, described in more detail below. Additionally, the top surface 112 of the cap 110 may be concave to further aid in gripping the medical plug 101. For example, a concave top surface 112 may increase the height ($H_P$) 220 of the raised protrusion 202 without increasing the profile of the cap 110. For example, the gripping member 130 may have a protrusion height ($H_P$) such that the protrusion and the outside edge 172 of the cap 110 are substantially planar. The gripping member 200 may advantageously assist in inserting and/or removing the medical plug 101. For example, the gripping member 200 may be adapted to transfer a rotational force in a twisting action to dislodge the medical plug 101 and facilitate removal of the medical plug 101.

Figure 5A:
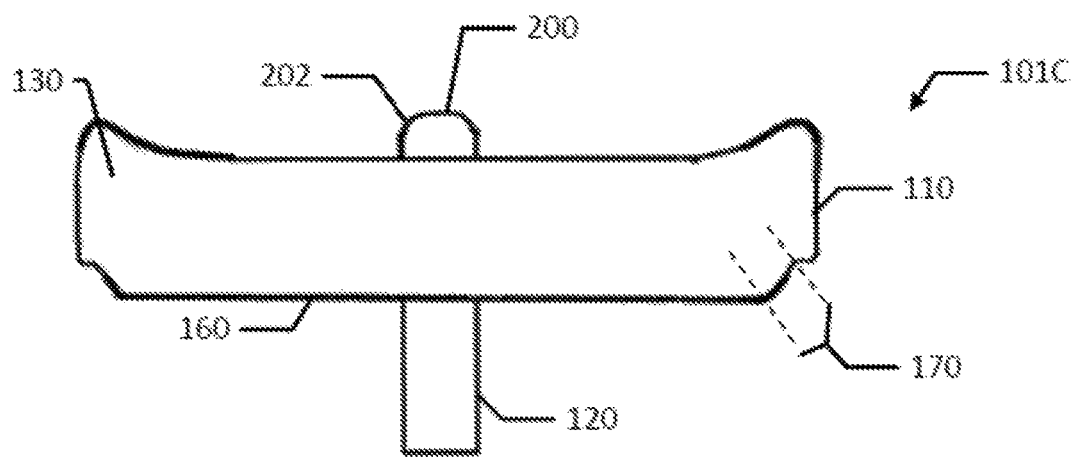
FIGS. 5A to 5D are side and top views of a medical plug, according to an example embodiment of the present disclosure.
Figure 5B:
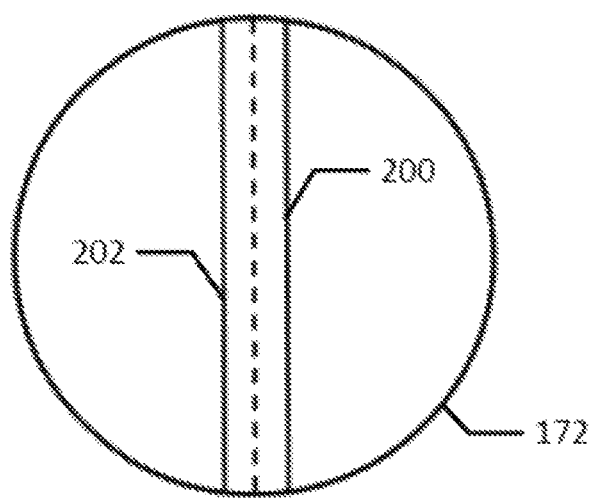
Figure 5C:
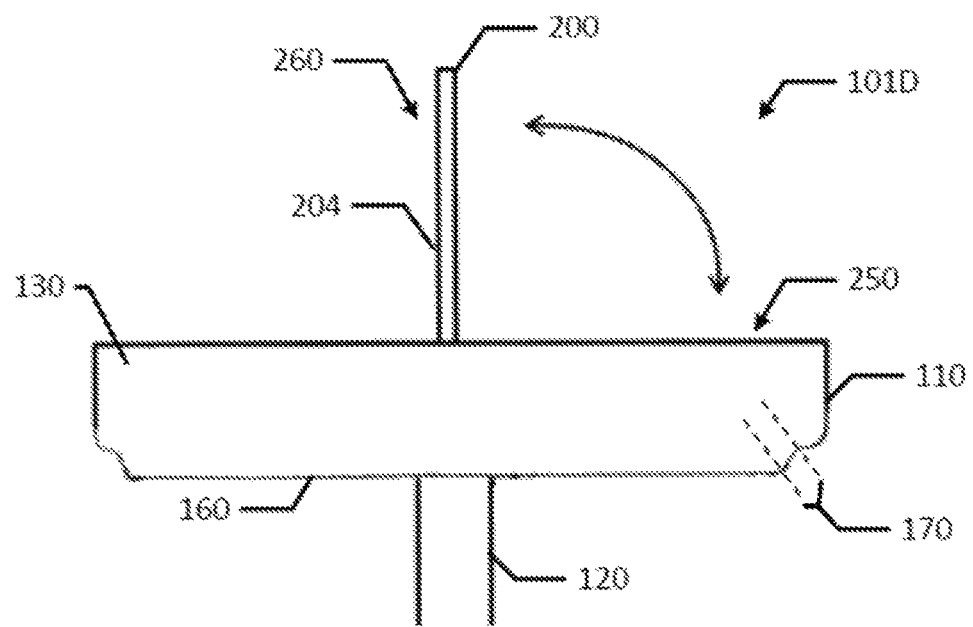
Figure 5D:
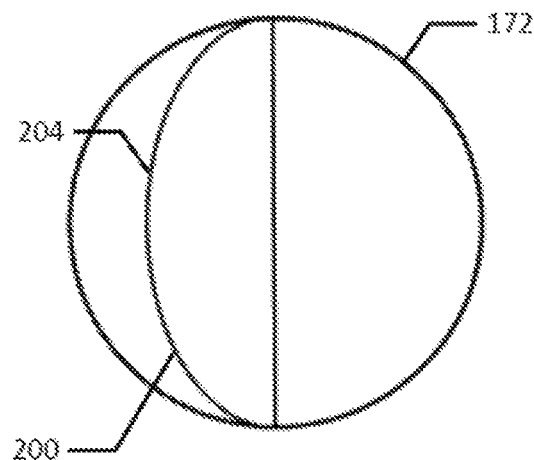

The raised protrusion 202 may be rectangular. In another example embodiment, the raised protrusion 202 may have other shapes and geometries. Additionally, the raised protrusion 202 may extend to the outer edge 172 of the cap 110. In other embodiments, the raised protrusion 202 may only partially extend along the top surface 112 of the cap 110. For example, the raised protrusion 202 may be tapered such that it has the largest height ($H_P$) 220 at the center of the cap 110 and has a gradually decreasing height ($H_P$) 220 as it approaches the outside edge 172 of the cap 110. Additionally, the gripping member 130 may included rounded corners (as illustrated in FIG. 5A) and other shape profiles that reduce.

Figure 4A:
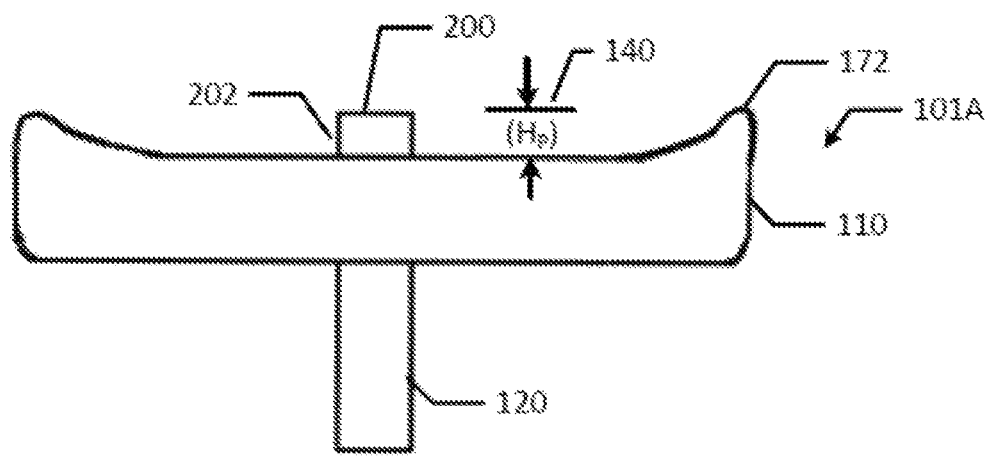
FIGS. 4A to 4D are side and top views of a medical plug, according to an example embodiment of the present disclosure.
Figure 4B:
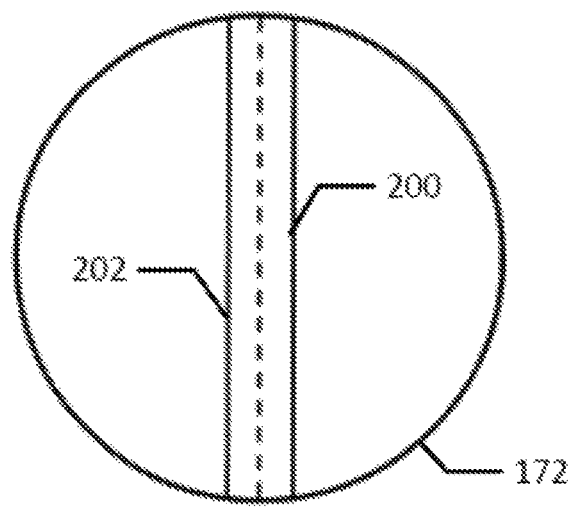
Figure 4C:
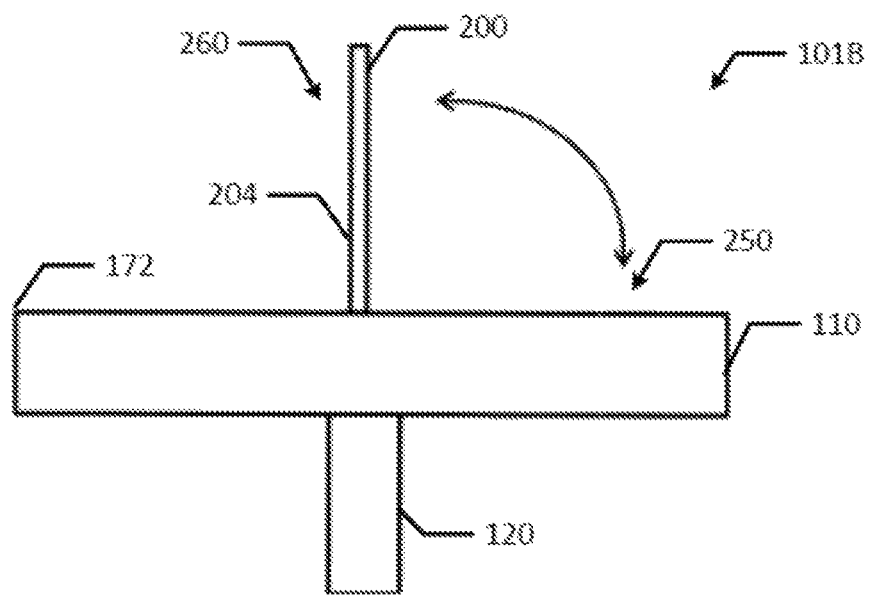
Figure 4D:
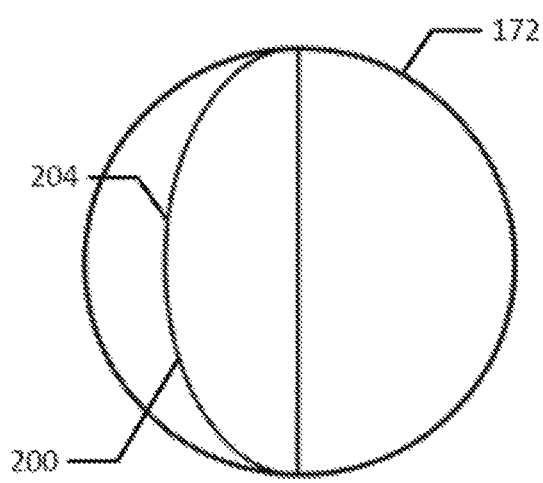

As illustrated in FIGS. 4C and 4D, the gripping member may include a flexible tab 204 attached to the top surface 112 of the cap 110. The flexible tab 204 may extend along a diameter of the cap 110. Additionally, the flexible tab 204 may be configured to lay flat against the top surface 112 of the cap 110 when in an inactive state 250 (e.g., not be used for removing the medical plug 101). In an example embodiment, the flexible tab 204 may be configured to pivot about the diameter of the cap 110 from a position substantially parallel with the top surface of the cap 110 (e.g., inactive state 250) to a position substantially perpendicular with the top surface of the cap 110 when in an active state 260 (e.g., used for removing the medical plug 101). In another example, the flexible tab 204 may pivot about a line that is offset from the diameter or centerline of the cap 110. The flexible tab 204 may be made of the same material as the cap 110 or may be made of a different material. Additionally, the flexible tab 204 may be formed by creating a thing material layer from an incision in the cap 110 parallel to the top surface 112 of the cap 110. For example, the cap 110 material may have suitable flexibility and strength such that a thin material layer may be used as the flexible tab 204. In an example, the flexible tab 204 may be made from a material such as a suitable copolyester, polyamide, polyethylene, polypropylene, polyacrylonitrile, or the like. An amorphous copolyester, polyamide, polyethylene, polypropylene, polyacrylonitrile, or similar material product typically has suitable appearance, clarity and mold release properties (usable with injection molding, for example). It also provides appropriate rigidity, toughness/durability, hydrolytic stability, heat resistance, and chemical resistance. Additionally, the cap 110 and flexible tab 204 may be made from one material, in a single mold, or multiple materials from several molds. For example, the flexible tab 204 may be attached to the cap 110 using adhesive, solvent bonding, radio-frequency (RF) welding and/or any other suitable means of affixing.

FIGS. 5A through 5D illustrate example embodiments of a medical plug apparatus 101C-D (generally referred to as medical plug 101). The medical plug apparatus 101 illustrated in FIGS. 5A through 5D may also include a shoulder 170, contact portion 160, and gripping portion 130 as discussed in relation to FIG. 2. For example, medical plug apparatus 101 may be similar to that described in FIGS. 4A through 4D and may also include a shoulder 170, a contact portion 160, and/or a gripping portion 130.

Figure 6A:
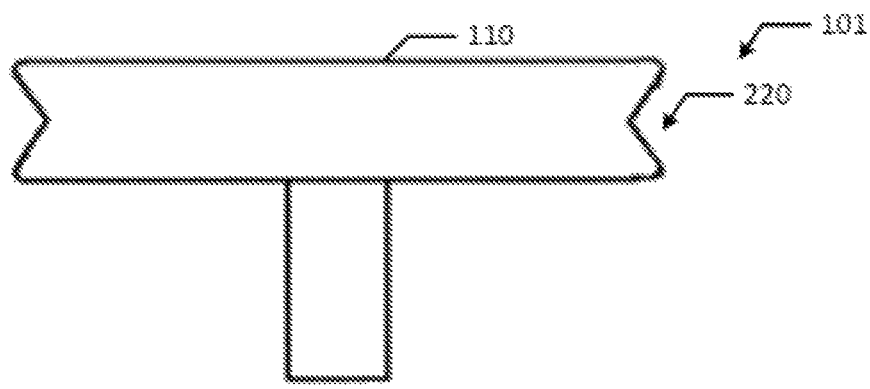
FIGS. 6A to 6C are side views of a medical plug, according to an example embodiment of the present disclosure.
Figure 6B:
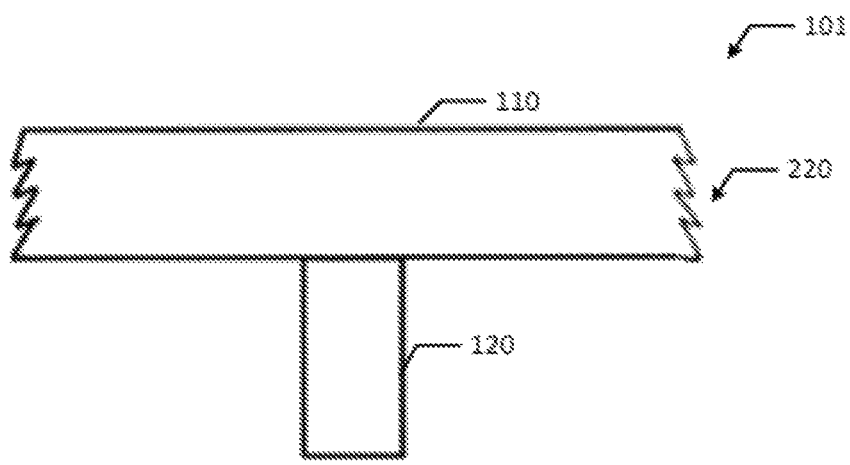
Figure 6C:
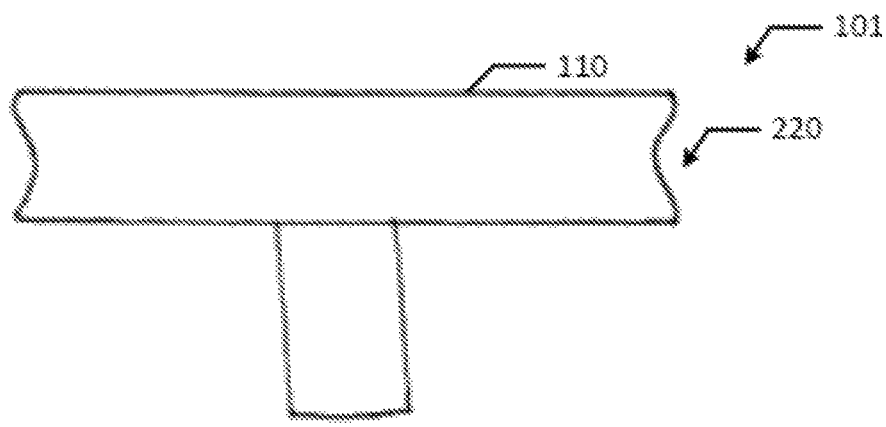

FIGS. 6A through 6C illustrate an example embodiment of a medical plug apparatus 101. As illustrated in the figures, the medical plug apparatus 101 may include additional gripping surfaces 220 on the cap 110. For example, as shown in FIG. 6A, the cap 110 may include a gripping surface 220, such as a notch gripping surface 220 that extends around the perimeter of the cap 110. In another example embodiment, the side of the cap 110 may be textured. For example, the side of the cap may include a ridged gripping surface 220 that is adapted to increase the friction between a clinician or patient's fingers and the cap 110 of the medical plug 101. In another example embodiment, the cap 110 may include a smooth recess gripping surface 220 along the perimeter of the cap 110, which may advantageously accept a clinician or patient's finger to assist with inserting and/or removing the medical plug 101.

Figure 7:
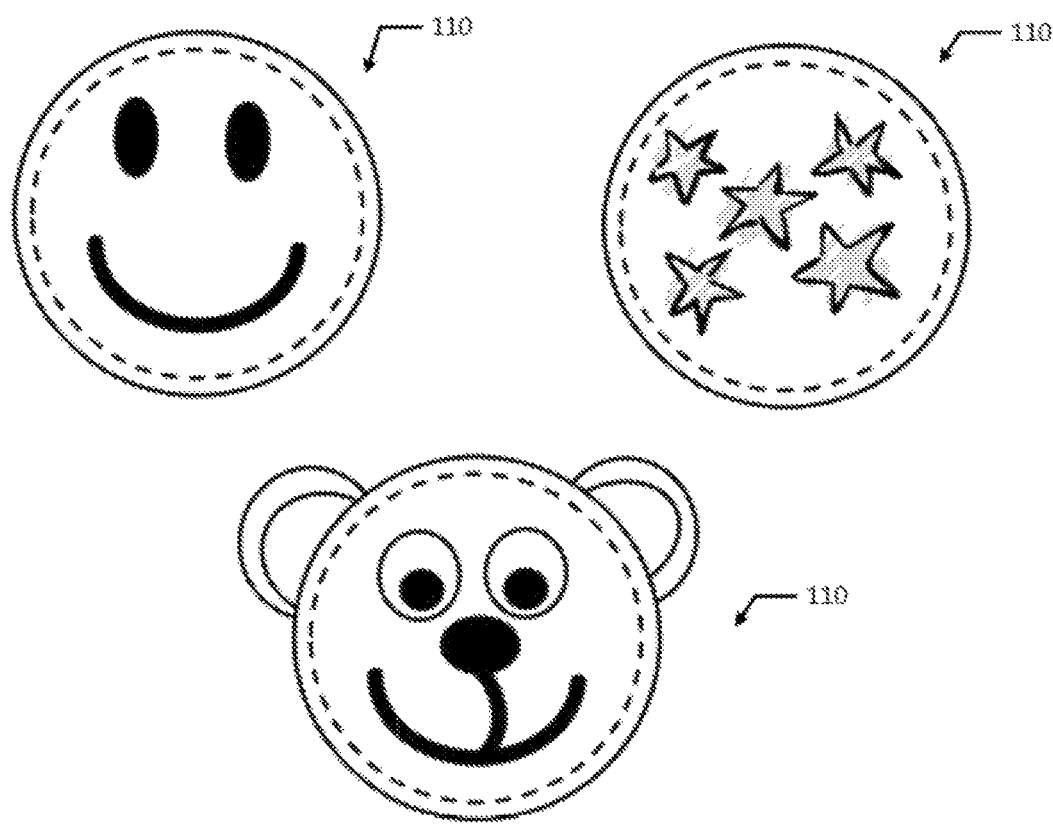
FIG. 7 is top view of a medical plug cap, according to an example embodiment of the present disclosure.

FIG. 7 illustrates example embodiments of a cap 110 of a medical plug apparatus 101. In some instances, especially with younger children, a patient may need encouragement to use the medical plug apparatus 101. For example, images and or specific shapes may be used on the cap 110 of the medical plug apparatus 101. In other example embodiments, the images and/or shapes may be included on other parts of the medical plug apparatus 101 and/or flexible bandage 103. In an example embodiment, the images and or shapes may provide positive psychological associations with a patient such that the image and/or shape is adapted to encourage use of the medical plug apparatus 101 and/or flexible bandage 103.

In an example embodiment, the images or shapes may be represented in one dimension. In other example embodiments, the images or shapes may be represented in multiple dimensions (e.g., two-dimensions or three-dimensions). The images or shapes may be selected based on age, gender, personal interest, etc. For example, a cap 110 may include the logo of a patient's favorite sports team. Additionally, the cap 110 may include a patient's favorite cartoon character, favorite animal, etc. In other example embodiments, the medical plug apparatus 101 may be colored to provide positive psychological associations with the patient. For example, the medical plug apparatus 101 may be colored red. The medical plug apparatus 101 may include other colorants and additives, such as glitter, or may glow in the dark to encourage use of the medical plug apparatus 101. In an example, the medical plug 101 may include one or more colorants that are adapted to contrast an outside environment, such as the floor, to reduce the likelihood of losing or misplacing the medical plug 101.

Figure 8:
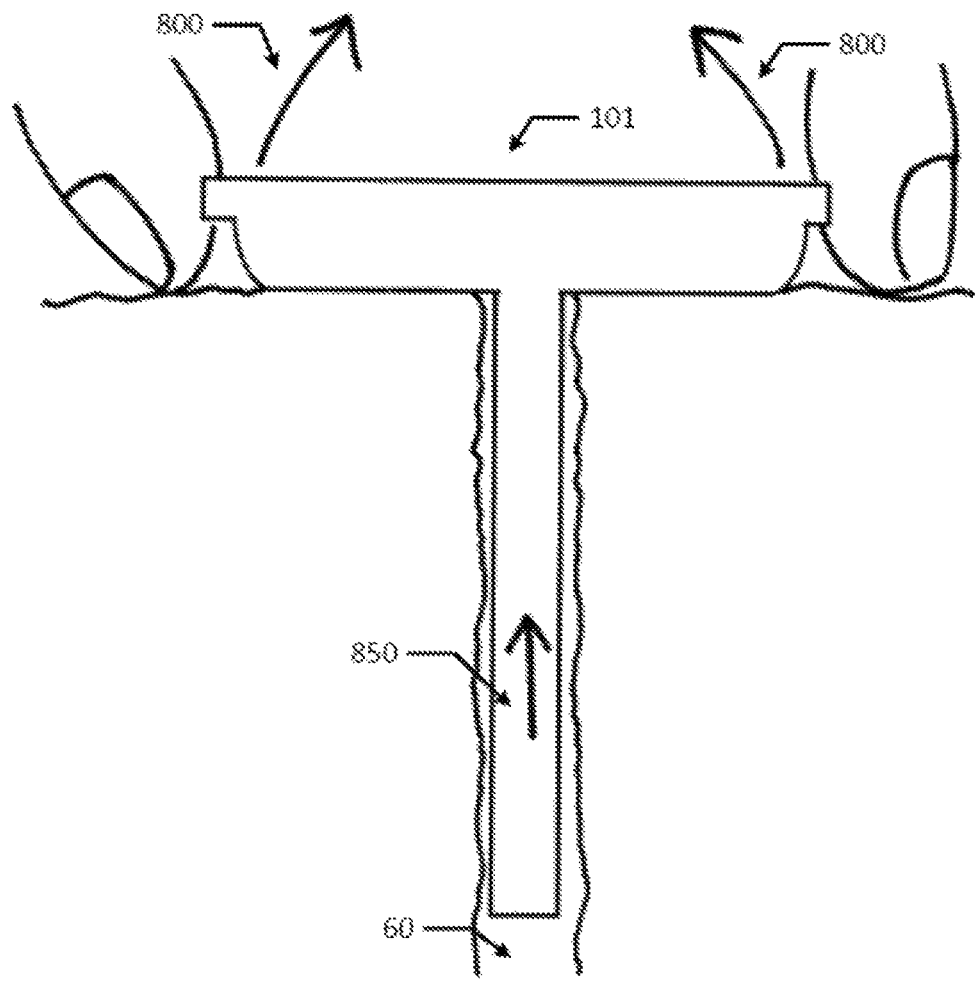
FIG. 8 is a cross-sectional view of a medical plug being removed from a stoma cavity, according to an example embodiment of the present disclosure.

FIG. 8 illustrates the removal of a medical plug 101 according to an example embodiment of the present disclosure. For example, a patient or clinician may position their fingers on the gripping portion 130 of the medical plug 101 such that, upon exerting a pulling force 800 on the first region 132 and the second region 134 of the gripping portion 130, the elongated cylindrical shaft 120 is directed outwardly away from the patient by the pulling force 800 causing a substantially axial tension force 850 on the elongated cylindrical shaft 120. For example, as the patient or clinician exerts a pulling force 800 on the cap 110, the outside edges of the cap 110 may slightly flex inward and translate the inward and upward pulling force 800 into a sufficient substantially axial tension force 850 to remove the medical plug 101 from a stoma cavity 60. For example, the gripping portion 130 may be specifically adapted (e.g., with a specific number of flanges 174, flange spacing, or gripping member) such that the pulling force 800 results in a substantially axial tension force 850 to prevent injury or discomfort to the patient. For example, non-axial tension forces may cause serious problems including necrosis, damage to the stoma cavity 60, or cause the patient other irritation and discomfort or injury. It should be appreciated that only a nominal pulling force 800 may be required to generate a sufficient substantially axial tension force 850 to remove the medical plug 101 from a stoma cavity 60.

Figure 9A:
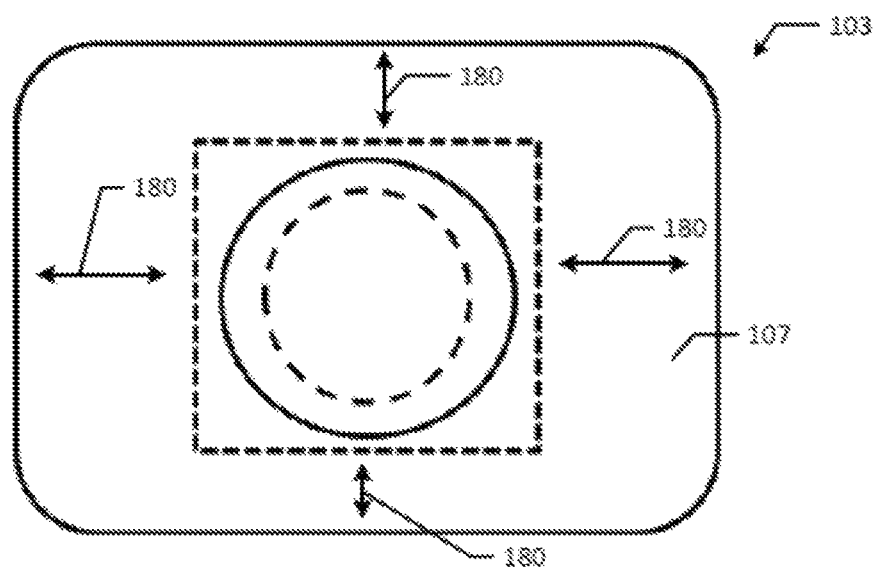
FIGS. 9A and 9B are a top view and a side view of an example flexible bandage, according to an example embodiment of the present disclosure.
Figure 9B:
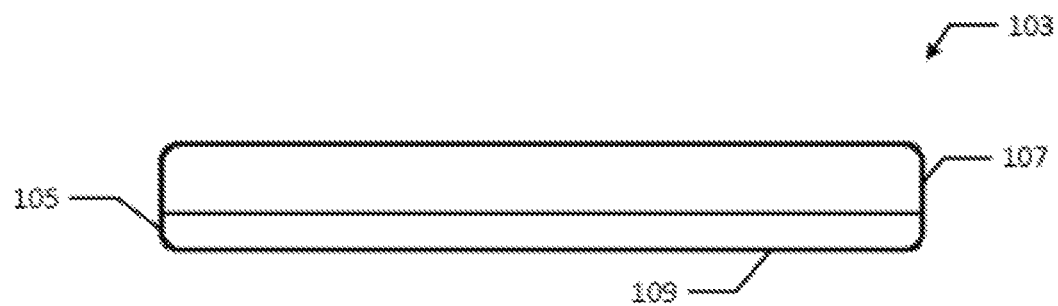

FIG. 9 illustrates an example embodiment of a flexible bandage 103. The flexible bandage may have an attachment side 105 and an exterior side 107. In an example embodiment, the attachment side 105 may include an adhesive coating 109. The adhesive coating 109 may include gelatin, pectin, and carboxy-methycelluslose. In another example, the adhesive coating 109 may be adapted to maintain moist conditions under the attachment side 105 of the bandage 103. Additionally, other suitable adhesives may be used that provide sufficient adhesion, biocompatibility, and longevity. The exterior side 107 may be smooth. For example, the exterior side 107 may have a texture that advantageously prevents the flexible bandage 103 from snagging or pulling on the patient's clothing or other external objects.

Additionally, the flexible bandage 103 may have a size and shape that is adapted to completely cover the cap 110 of the medical plug 101. For example, the flexible bandage 103 includes a peripheral portion 180 extending beyond the entire outside edge 172 of the cap 110. The peripheral portion 180 may sized to ensure that the flexible bandage 103 has enough surface area to form a solid adhesive bond with the patient's skin. In an example embodiment, the adhesive coating 109 on the attachment side 105 of the peripheral portion 180 enables the flexible bandage 103 to adhere to the patient and form a barrier between the outside edge 172 of the cap 110 and the outside environment. The flexible bandage 103 may be opaque. In other example embodiments, the flexible bandage 103 may be clear or colored. For example, as discussed above, the flexible bandage may be colored or include an image that is pleasing to the patient.

Figure 10:
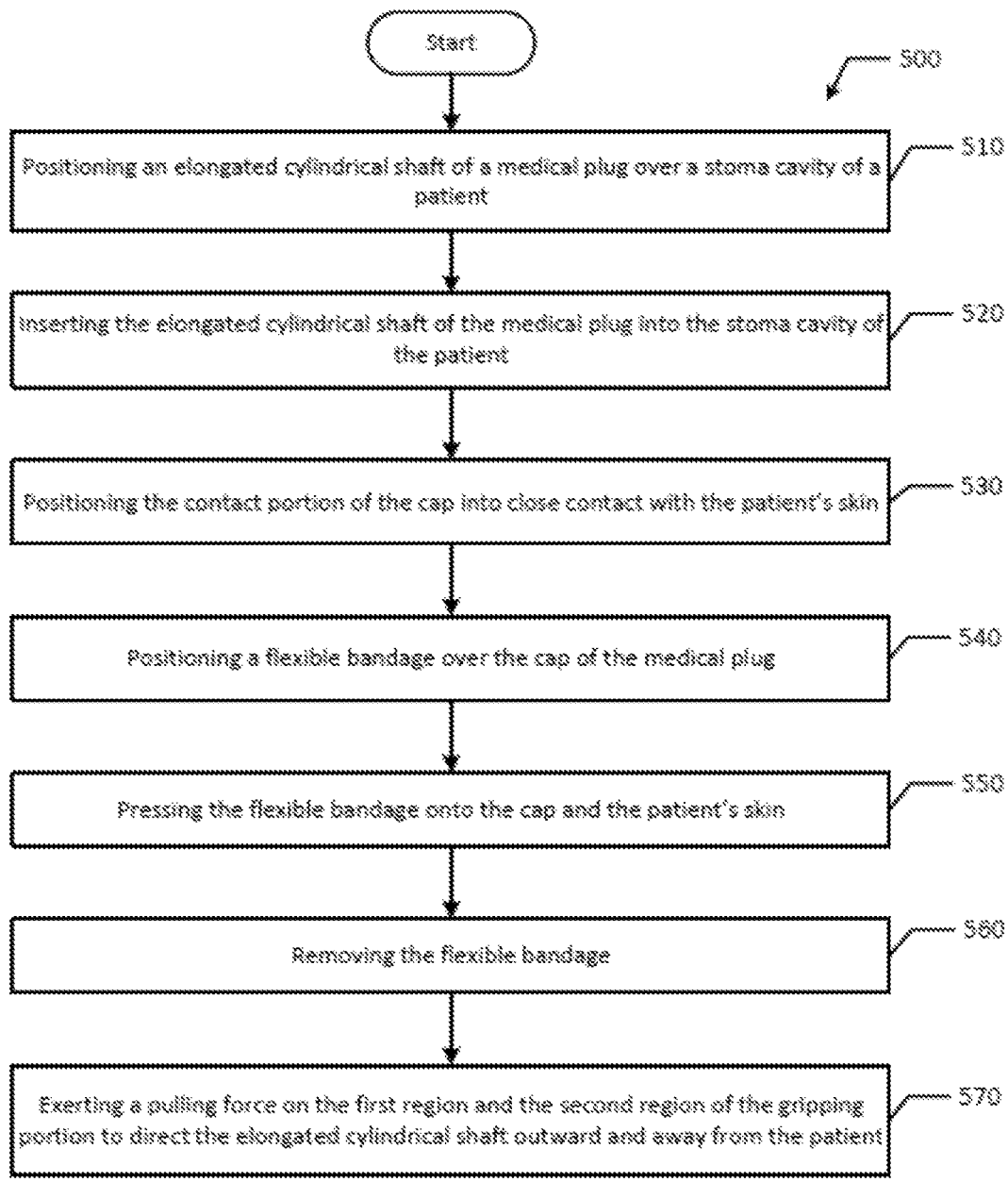
FIG. 10 is a flowchart of an example insertion and removal process using a stoma assembly.

FIG. 10 includes a flowchart of an example insertion and removal process 500 using a medical plug 101 and flexible bandage 103. Although process 500 is described with reference to the flowchart illustrated in FIG. 10, it will be appreciated that many other methods and sequencing of performing the acts associated with the process 500 may be used. For example, the order of many of the blocks may be changed, many blocks may be intermittently repeated or continually performed, certain blocks may be combined with other blacks, and many of the blocks described are optional or may only be contingently performed.

The example process 500 may begin with a clinician or patient positioning an elongated cylindrical shaft 120 over a stoma cavity 60 of the patient (block 510). Then, the clinician or patient may insert the elongated cylindrical shaft 120 of the medical plug 101 into the stoma cavity 60 of the patient (block 520). In an example embodiment, the distal end 127 of the cylindrical shaft 120 may be rounded to assist in positioning and inserting the shaft 120 within the stoma cavity 60. Additionally, the cylindrical shaft 120 may include a smooth external surface 120 to reduce injury. The patient or clinician may coat the cylindrical shaft 120 with a lubricant, such as a water soluble lubricant before insertion. Once the cylindrical shaft 120 is inserted, the clinician or patient may position the contact portion 160 of the cap 110 into close contact with the patient's skin (block 530). In an example, the bottom surface 114 and/or the contact portion 160 of the cap is adapted to create a seal with a layer of skin to prevent contaminants from entering the stoma cavity 60. Then, the clinician or patient may position a flexible bandage over the cap 110 of the medical plug 101 (block 540). For example, the clinician or patient may position the flexible bandage 103 such that the medical plug is centered under the bandage 103 (e.g., there is a sufficient peripheral portion 180 around all sides of the medical plug 101). Then, the clinician or patient may press the flexible bandage 103 onto the cap 110 and the patient's skin (block 550). The bandage 103 may include an attachment side 105 with an adhesive coating 109. For example, the adhesive coating may include gelatin, pectin, and carboxy-methycelluslose such that it maintains most conditions under the attachment side 105 of the bandage 103. After some time, the patient or clinician may remove the flexible bandage 103 (block 560). Then, the patient or clinician may exert a pulling force 800 on the first region 132 and the second region 134 of the gripping portion 130 to direct the elongated cylindrical shaft 120 outward and away from the patient (block 570). Additionally, the patient or clinician may exert a pulling force on a gripping member 200 or other gripping surfaces 220 on the medical plug 101. In an example, the clinician or patient may twist and/or rotate the cap 110 to dislodge the medical plug 101 through radial force acting perpendicular to the smooth surface 122 of the elongated cylindrical shaft 120. The radial force may interact between the cylindrical shaft 120 and the stoma cavity 60 to loosen the medical plug 101 from the stoma cavity 60.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Also, it should be appreciated that the features of the dependent claims may be embodied in the systems, methods, and apparatus of each of the independent claims.

What is claimed is:

1. A medical plug apparatus for use in conjunction with an ostomy procedure, the medical plug apparatus comprising
a cap having a top surface, a bottom surface, and a first thickness, wherein the bottom surface comprises a side portion of the cap and a bottom face of the cap; and
a flexible, elongated cylindrical shaft extending orthogonally away from the bottom surface of the cap from a proximal end to a distal end, wherein
the first thickness extends from the top surface to the bottom surface at the proximal end of the elongated cylindrical shaft,
the elongated cylindrical shaft has a smooth external surface, a shaft diameter, and a shaft length, the shaft diameter and the shaft length adapted to plug a stoma cavity upon inserting the elongated cylindrical shaft into the stoma cavity, the bottom surface of the cap includes a gripping portion on the side portion of the cap, a contact portion on the bottom face of the cap, and a shoulder on a side portion of the cap between the gripping portion and the contact portion, the shoulder extends around a periphery of the contact portion, the gripping portion includes a first region, a second region, and a second thickness, the gripping portion extends from the top surface to the shoulder portion, the second thickness extends from the top surface to the gripping portion at the shoulder, the second thickness is less than the first thickness, the gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft, the contact portion includes a contact diameter, the contact portion extends from the shoulder across the bottom surface of the cap to the proximal end of the elongated cylindrical shaft, the shoulder includes a third thickness, the third thickness extends from the gripping portion at the shoulder to the contact portion, the third thickness is less than the first thickness, the gripping diameter is larger than the contact diameter and a diameter of the shoulder portion, and the contact portion is adapted to create a seal with a layer of skin of a patient.

2. The medical plug apparatus of claim 1, wherein the medical plug is made of silicone that includes a colorant adapted to contrast an outside environment.

3. The medical plug apparatus of claim 1, wherein at least a portion of the top surface of the cap is textured.

4. The medical plug apparatus of claim 3, wherein the top surface of the cap includes at least one of embossing and debossing.

5. The medical plug apparatus of claim 1, wherein the top surface of the cap includes a gripping member.

6. The medical plug apparatus of claim 5, wherein
the cap includes an outside edge,
the top surface of the cap is concave,
the gripping member includes a raised protrusion extending along a diameter of the cap,
the gripping member is adapted to transfer a rotational force in a twisting action to dislodge the medical plug and facilitate removal of the medical plug apparatus, and
the gripping member has a protrusion height such that the protrusion and the outside edge of the cap are substantially planar.

7. The medical plug apparatus of claim 6, wherein the raised protrusion is rectangular and the raised protrusion extends to the outside edge of the cap.

8. The medical plug apparatus of claim 5, wherein the gripping member includes a flexible tab attached to the top surface of the cap, the flexible tab extends along a diameter of the cap, the flexible tab is configured to lay flat against the top surface of the cap when in an inactive state, and the flexible tab is configured to rotate axially about the diameter to a position substantially perpendicular with the top surface of the cap when in an active state.

9. The medical plug apparatus of claim 1, wherein the gripping portion includes at least two flanges spaced equidistant about the perimeter of the cap.

10. The medical plug apparatus of claim 9, wherein a first shoulder of a first flange is separate from a second shoulder of a second flange.

11. The medical plug apparatus of claim 1, wherein the shaft length is determined based on the patient's body weight.

12. The medical plug apparatus of claim 1, wherein the distal end of the elongated cylindrical shaft is rounded.

13. The medical plug apparatus of claim 1, wherein the cap includes at least one image, wherein the at least one image is selected based on positive psychological associations with the patient, and the at least one image is adapted to encourage use of the medical plug apparatus.

14. The medical plug apparatus of claim 1, wherein the cap forms a multi-dimensional image, wherein the multi-dimensional image is adapted to encourage use of the medical plug apparatus due to positive psychological associations with the patient.

15. A stoma assembly comprising:
a medical plug comprising:
a cap having a top surface, a bottom surface, and a first thickness, wherein the bottom surface comprises a side portion of the cap and a bottom face of the cap; and
a flexible, elongated cylindrical shaft extending orthogonally away from the bottom surface of the cap from a proximal end to a distal end, wherein
the first thickness extends from the top surface to the bottom surface at the proximal end of the elongated cylindrical shaft,
the elongated cylindrical shaft has a smooth external surface, a shaft diameter, and a shaft length, the shaft diameter and the shaft length adapted to plug a stoma cavity upon inserting the elongated cylindrical shaft into the stoma cavity,
the bottom surface of the cap includes a gripping portion on the side portion of the cap, a contact portion on the bottom face of the cap, and a shoulder on a side portion of the cap between the gripping portion and the contact portion,
the shoulder extends around a periphery of the contact portion,
the gripping portion includes a first region, a second region, and a second thickness,
the gripping portion extends from the top surface to the shoulder portion,
the second thickness extends from the top surface to the gripping portion at the shoulder,
the second thickness is less than the first thickness,
the gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft,
the contact portion includes a contact diameter, the contact portion extends from the shoulder across the bottom surface of the cap to the proximal end of the elongated cylindrical shaft,
the shoulder includes a third thickness,
the third thickness extends from the gripping portion at the shoulder to the contact portion,
the third thickness is less than the first thickness, the gripping diameter is larger than the contact diameter and a diameter of the shoulder portion, and the contact portion is adapted to create a seal with a layer of skin of a patient; and a flexible bandage having an attachment side and an exterior side, wherein the attachment side includes an adhesive coating, the exterior side is smooth, the flexible bandage has a size and shape that is adapted to completely cover the cap of the medical plug, and the flexible bandage includes a peripheral portion extending beyond the entire outside edge of the cap, wherein the adhesive coating on the attachment side of the peripheral portion enables the flexible bandage to adhere to the patient and form a barrier between the outside edge of the cap and the outside environment.

16. The stoma assembly of claim 15, wherein the bandage is opaque.

17. The stoma assembly of claim 15, wherein the adhesive coating includes gelatin, pectin, and carboxy-methylcellulose.

18. The stoma assembly of claim 15, wherein the adhesive coating is adapted to maintain moist conditions under the attachment side of the bandage.

19. A method comprising:

positioning a flexible, elongated cylindrical shaft of a medical plug over a stoma cavity of a patient;

inserting the elongated cylindrical shaft of the medical plug into the stoma cavity of a patient, wherein the medical plug includes a cap having a top surface, a bottom surface, and a first thickness, the elongated cylindrical shaft extends orthogonally away from the bottom surface of the cap from a proximal end to a distal end, wherein the bottom surface comprises a side portion of the cap and a bottom face of the cap, the first thickness extends from the top surface to the bottom surface at the proximal end of the elongated cylindrical shaft, the elongated cylindrical shaft has a smooth external surface, a shaft diameter, and a shaft length, the shaft diameter and the shaft length, the shaft diameter and the shaft length adapted to plug a stoma cavity upon inserting the elongated cylindrical shaft into the stoma cavity, the bottom surface of the cap includes a gripping portion on the side portion of the cap, a contact portion on the bottom face of the cap, and a shoulder on a side portion of the cap between the gripping portion and the contact portion, and the shoulder extends around a periphery of the contact portion;

positioning the contact portion of the cap into close contact with the patient's skin by applying a downward pressure to the top surface of the cap, wherein the contact portion includes a contact diameter, the contact portion extends from the shoulder across the bottom surface of the cap to the proximal end of the elongated cylindrical shaft, the shoulder includes a third thickness, the contact portion is adapted to create a seal with a layer of skin of a patient, the third thickness extends from the gripping portion at the shoulder to the contact portion, the third thickness is less than the first thickness, the gripping portion includes a first region, a second region, and a second thickness, the gripping portion extends from the top surface to the shoulder portion, the second thickness extends from the top surface to the gripping portion at the shoulder, and the second thickness is less than the first thickness; and exerting a pulling force on the first region and the second region of the gripping portion, to direct the elongated cylindrical shaft outward and away from the patient, wherein the gripping portion has a gripping diameter such that, upon exerting a pulling force on the first region and the second region of the gripping portion, the elongated cylindrical shaft is directed outwardly away from the patient by the pulling force causing a substantially axial tension force on the elongated cylindrical shaft, and the gripping diameter is larger than the contact diameter and a diameter of the shoulder portion.

20. The method of claim 19, further comprising rotating the cap to dislodge the medical plug, wherein the cap includes an outside edge, the top surface of the cap is concave, the top surface of the cap includes a gripping member, the gripping member includes a raised protrusion extending along a diameter of the cap, the gripping member is adapted to transfer a rotational force in a twisting action to dislodge the medical plug and facilitate removal of the medical plug, and the gripping member has a protrusion height such that the protrusion and the outside edge of the cap are substantially planar.

* * * * *